United States Patent
Cox et al.

(10) Patent No.: US 6,599,905 B2
(45) Date of Patent: Jul. 29, 2003

(54) PYRAZINE COMPOUNDS

(75) Inventors: Brian Cox, Bedford (GB); Dean David Edney, London (GB); Michael Simon Loft, London (GB); Malcolm Stuart Nobbs, Stevenage (GB); Gita Punjabhai Shah, London (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/855,703

(22) Filed: May 16, 2001

(65) Prior Publication Data
US 2002/0169172 A1 Nov. 14, 2002

Related U.S. Application Data

(62) Division of application No. 09/380,062, filed as application No. PCT/EP98/01077 on Feb. 26, 1998, now Pat. No. 6,255,307.

(30) Foreign Application Priority Data

Mar. 1, 1997 (GB) ............................. 9704275
Apr. 23, 1997 (GB) ............................. 9708183

(51) Int. Cl.[7] .................. A61K 31/4965; A61K 31/496; A61K 31/497
(52) U.S. Cl. ........................... 514/255.06; 514/252.11; 514/255.05
(58) Field of Search ............... 514/252.11, 255.05, 514/255.06

(56) References Cited

U.S. PATENT DOCUMENTS 4,402,958 A 9/1983 Izzo

FOREIGN PATENT DOCUMENTS

PH 26444 7/1992

OTHER PUBLICATIONS

Hewitt et al., Brain Research, 898(2), p. 281–287 (2001) (Medline Abstract).*
Rosen et al. Drug and Alcohol Dependence 52, pp. 173–176 (1998).*
Abstract for Phillipines 26444 (Jul. 1992).
Chemical Abstracts, vol. 97, No. 28, 1982, Columbus Ohio, US. Abstract No. 110034z, p. 617 and JP 08 238 778 A.Mar. 1982.
Lakhan, "Novel Synthesis of Heterocycles fom A–Oxonitroles; Part III", Synthesis, vol. 10, Oct. 1987, Stuttgart, De, pp. 914–915.

* cited by examiner

Primary Examiner—Emily Bernhardt
(74) Attorney, Agent, or Firm—Nixon & Vanderhye P.C.

(57) ABSTRACT

Compounds of formula (I)

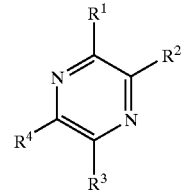

(I)

where $R^1$ is phenyl substituted by one or more halogen atoms, naphthyl and naphthyl substituted by one or more halogen atoms; $R^2$ is —$NH_2$ and —$NHC(=O)R^a$; $R^3$ is —$NR^bR^c$, —$NHC(=O)R^a$ or hydrogen; $R^4$ is hydrogen, —$C_{1-4}$ alkyl, —CN, —$CH_2OH$, —$CH_2OR^d$, —$CH_2S(O)_xR^d$ and —$C_{1-4}$ alkyl substituted by one or more halogen atoms in which $R^a$ represents $C_{1-4}$ alkyl or $C_{3-7}$ cycloalkyl, and $R^b$ and $R^c$, which may be the same or different, are hydrogen or $C_{1-4}$ alkyl, or together with the nitrogen atom to which they are attached, form a 6-membered nitrogen containing heterocycle, which heterocycle can be further substituted with one or more $C_{1-4}$ alkyl; $R^d$ is $C_{1-4}$ alkyl or $C_{1-4}$ alkyl substituted by one or more halogen atoms; x is an integer zero, one or two; and salts, solvates and prodrugs thereof, provided that $R^1$ does not represent:

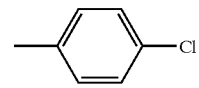

when $R^2$ is —$NH_2$, and both $R^3$ and $R^4$ are hydrogen. The compounds are useful as analgesics, anticonvulsants, for treating bipolar disorder and as neuroprotectants.

7 Claims, No Drawings

PYRAZINE COMPOUNDS

This is a division of application Ser. No. 09/380,062, filed Aug. 25, 1999, now U.S. Pat. No. 6,255,307, which is a 371 of PCT/EP98/01077, filed Feb. 26, 1998, the entire content of which is hereby incorporated by reference in this application.

The present invention relates to a class of pyrazine compounds which are useful in the treatment of central nervous system (CNS) diseases and disorders and to their pharmaceutically acceptable derivatives, pharmaceutical compositions containing them, to their use in the treatment of such disorders and to methods of preparing them.

Numerous phenyl pyrazine derivatives are known in the prior art. For example, Synthesis (1987), (10), 914–915, describes phenyl pyrazine derivatives including, inter alia, 3-(4-chlorophenyl)-pyrazinamine. No pharmaceutical utility is however described in that prior art document.

The present invention relates to a series of pyrazine derivatives which are sodium channel blockers. These compounds are particularly good anti-convulsants and as such are useful in the treatment of CNS diseases such as epilepsy.

Accordingly, the invention provides a compound of formula (I)

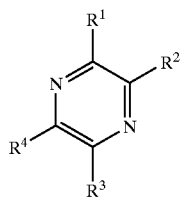

wherein
$R^1$ is selected from the group consisting of phenyl substituted by one or more halogen atoms, naphthyl and naphthyl substituted by one or more halogen atoms;
$R^2$ is selected from the group consisting of —$NH_2$ and —NHC((=O))$R^a$;
$R^3$ is selected from the group consisting of —$NR^bR^c$, —NHC((=O))$R^a$ and hydrogen;
$R^4$ is selected from the group consisting of hydrogen, —$C_{1-4}$ alkyl (preferably methyl), —$C_{1-4}$ alkyl (preferably methyl) substituted by one or more halogen atoms, —CN, —$CH_2OH$, —$CH_2OR$ and —$CH_2S(O)_xR^d$;
wherein
$R^a$ represents $C_{1-4}$ alkyl or $C_{3-7}$ cycloalkyl, and
$R^b$ and $R^c$, which may be the same or different, are selected from hydrogen and $C_{1-4}$ alkyl, or together with the nitrogen atom to which they are attached, form a 6-membered nitrogen containing heterocycle, which heterocycle can be further substituted with one or more $C_{1-4}$ alkyl;
$R^d$ is selected from $C_{1-4}$ alkyl or $C_{1-4}$ alkyl substituted by one or more halogen atoms;
x is an integer zero, one or two;
and pharmaceutically acceptable derivatives thereof;
with the proviso that $R^1$ does not represent;

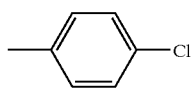

when $R^2$ is —$NH_2$, and both $R^3$ and $R^4$ are hydrogen.

By pharmaceutically acceptable derivative is meant any pharmaceutically acceptable salt or solvate of the compounds of formula (I), or any other compound which upon administration to the recipient is capable of providing (directly or indirectly) a compound of formula (I) or an active metabolite or residue thereof (eg. a prodrug). Reference hereinafter to the compounds of formula (I) includes the compound of formula (I) and pharmaceutically acceptable derivatives thereof.

Suitable prodrugs are well-known in the art and include N-acyl derivatives, for example at any of the nitrogens in the compounds of formula (I), for example simple acyl derivatives such as acetyl, propionyl and the like or groups such as R—O—$CH_2$-nitrogen or R—O—C(O)-nitrogen.

As used herein, the term halogen atom includes fluorine, chlorine, bromine or iodine.

The term $C_{1-4}$alkyl as used herein includes straight chained and branched alkyl groups containing 1 to 4 carbon atoms, and in particular includes methyl and isopropyl.

The term $C_{3-7}$cycloalkyl includes groups containing 3 to 7 carbon atoms, and in particular includes cyclopropyl.

The term heterocycle as used herein includes 6 membered heterocycles containing at least one nitrogen heteroatom, and preferably two nitrogen heteroatoms. A particularly suitable heterocycle is piperazinyl.

$R^1$ is aptly selected from unsubstituted naphthyl and phenyl substituted by one or more halogen atoms. Particularly $R^1$ represents phenyl substituted by more than one halogen atom, such as di- or tri-halogenated phenyl. Preferably, the halogen substituent in $R^1$ is chloro. Suitably $R^1$ is selected from 2,3,5-trichlorophenyl, 2,3-dichlorophenyl, 2,5-dichlorophenyl, 1-naphthyl and 2-naphthyl. In particular, $R^1$ is 2,3,5-trichlorophenyl.

Suitably $R^2$ is selected from —$NH_2$, isopropylcarbonylamino and cyclopropylcarbonylamino. $R^2$ is preferably —$NH_2$.

Suitably $R^3$ is selected from hydrogen, —$NH_2$, dimethylamino, 4-methyl-1-piperazinyl, acetamido, isopropylcarbonylamino, cyclopropylcarbonylamino. $R^3$ is preferably —$NH_2$.

Suitably $R^4$ is selected from hydrogen, —CN, —$CH_2OH$ or methyl. $R^4$ is preferably —$CH_2OH$ or, more preferably, hydrogen.

More preferably, $R^2$ and $R^3$ are both —$NH_2$.

A preferred class of compounds of formula (I) includes those wherein $R^1$, $R^2$ and $R^3$ are as defined above and $R^4$ is selected from the group consisting of hydrogen, —$C_{1-4}$ alkyl (preferably methyl) and —$C_{1-4}$ alkyl (preferably methyl) substituted by one or more halogen atoms.

A preferred compound of formula (I) is wherein $R^1$ is 2,3,5-trichlorophenyl; $R^2$ is —$NH_2$; $R^3$ is —$NH_2$; and $R^4$ is hydrogen.

According to a particular embodiment of the present invention, there is provided a compound of formula (Ia)

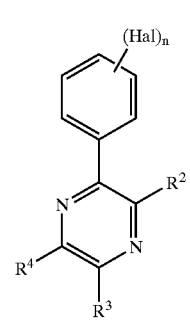

wherein

Hal represents a halogen atom selected from fluorine, chlorine, bromine and iodine;
n is 2 or 3;
$R^2$ is selected from the group consisting of —$NH_2$ and —NHC((=O))$R^a$;
$R^3$ is selected from the group consisting of —$NR^bR^c$, —NHC((=O))$R^a$ and hydrogen;
$R^4$ is selected from the group consisting of hydrogen, —$C_{1-4}$ alkyl (preferably methyl), —$C_{1-4}$ alkyl (preferably methyl) substituted by one or more halogen atoms, —CN, —$CH_2OH$, $CH_2OR^d$ and —$CH_2S(O)_xR^d$;
wherein
$R^a$ represents $C_{1-4}$ alkyl or $C_{3-7}$cycloalkyl, and
$R^b$ and $R^c$, which may be the same or different, are selected from hydrogen and $C_{1-4}$ alkyl, or together with the nitrogen atom to which they are attached, form a 6-membered nitrogen containing heterocycle, which heterocycle can be further substituted with one or more $C_{1-4}$ alkyl;
$R^d$ is selected from $C_{1-4}$ alkyl or $C_{1-4}$ alkyl substituted by one or more halogen atoms;
x is an integer zero, one or two;
and pharmaceutically acceptable derivatives thereof.

It will be appreciated that $R^2$, $R^3$ and $R^4$ as defined above for formula (Ia), are substantially as hereinbefore described with reference to formula (I).

Particulary appropriately in formula (Ia), $R^2$ and $R^3$ both represent —$NH_2$. Aptly $R^4$ represents —CN, methyl or, more appropriately, —$CH_2OH$ or, even more appropriately, hydrogen.

Aptly Hal in formula (Ia) represents chlorine. Suitably n is 3, and appropriately the resulting tri-substitution represents a compound of the following formula (Ib)

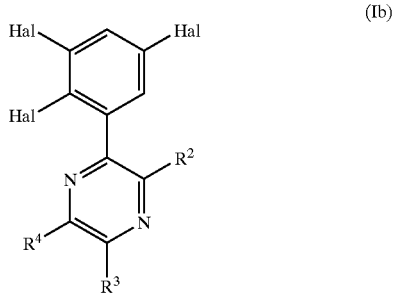

(Ib)

wherein $R^2$, $R^3$ and $R^4$ are substantially as defined above with reference to formula (Ia);
and pharmaceutically acceptable derivatives thereof.

Preferred compounds of the present invention are
2,6-diamino-3-(2,3-dichlorophenyl)pyrazine,
2,6-diamino-3-(2,5-dichlorophenyl)pyrazine,
2,6-diamino-3-(1-naphthyl)pyrazine,
2,6-diamino-3-(2-naphthyl)pyrazine,
2-amino-6-(4-methyl-piperazinyl)-3-(2,3,5-trichlorophenyl)pyrazine,
2-amino-6-dimethylamino-3-(2,3-dichlorophenyl)pyrazine,
2-amino-6-dimethylamino-3-(1-naphthyl)pyrazine,
2,6-dicyclopropylcarbonylamino-3-(2,3,5-trichlorophenyl)pyrazine,
2-amino-6-cyclopropylcarbonylamino-3-(2,3,5-trichlorophenyl)pyrazine,
2,6-diisopropylcarbonylamino-3-(2,3,5-trichlorophenyl)pyrazine,
2-amino-6-isopropylcarbonylamino-3-(2,3,5-trichlorophenyl)pyrazine,
2-isopropylcarbonylamino-6-amino-3-(2,3,5-trichlorophenyl)pyrazine,
2-cyclopropylcarbonylamino-6-amino-3-(2,3,5-trichlorophenyl)pyrazine,
2-amino-6-acetamido-3-(2,3,5-trichlorophenyl)pyrazine,
2-amino-6-acetamido-3-(2,5-dichlorophenyl)pyrazine,
2-amino-6-acetamido-3-(2-naphthalene)pyrazine,
5-methyl-2,6-Diamino-3-(2,3,5-trichlorophenyl)pyrazine,
5-cyano-2,6-Diamino-3-(2,3,5-trichlorophenyl)pyrazine,
and pharmaceutically acceptable derivatives thereof.

Further preferred is the compound 5-hydroxymethyl-2,6-diamino-3-(2,3,5-trichlorophenyl)pyrazine and pharmaceutically acceptable derivatives thereof.

A particularly preferred compound according to the present invention is 2,6-diamino-3-(2,3,5-trichlorophenyl)pyrazine and pharmaceutically acceptable derivatives thereof.

It is to be understood that the present invention covers all combinations of particular and preferred groups described herein above.

The compounds of formula (I) are particularly useful as anticonvulsants. They are therefore useful in treating epilepsy. They may be used to improve the condition of a host, typically a human being, suffering from epilepsy. They may be employed to alleviate the symptoms of epilepsy in a host. "Epilepsy" is intended to include the following seizures:— simple partial seizures, complex partial seizures, secondary generalised seizures, generalised seizures including absence seizures, myoclonic seizures, clonic seizures, tonic seizures, tonic clonic seizures and atonic seizures.

The compounds of formula (I) are additionally useful in the treatment of bipolar disorder, alternatively known as manic depression. Type I or II bipolar disorder may be treated. The compounds of formula (I) may thus be used to improve the condition of a human patient suffering from bipolar disorder. They may be used to alleviate the symptoms of bipolar disorder in a host. The compounds of formula (I) may also be used in the treatment of unipolar depression.

The compounds of formula (I) are useful as analgesics. They are therefore useful in treating or preventing pain. They may be used to improve the condition of a host, typically a human being, suffering from pain. They may be employed to alleviate pain in a host. Thus, the compounds of formula (I) may be used as a preemptive analgesic to treat acute pain such as musculoskeletal pain, post operative pain and surgical pain, chronic pain such as chronic inflammatory pain (e.g. rheumatoid arthritis and osteoarthritis), neuropathic pain (e.g. post herpetic neuralgia, trigeminal neuralgia and sympathetically maintained pain) and pain associated with cancer and fibromyalgia. The compounds of formula (I) may also be used in the treatment or prevention of pain associated with migraine.

The compounds of formula (I) are further useful in the treatment of functional bowel disorders which include non-ulcer dyspepsia, non-cardiac chest pain and in particular irritable bowel syndrome. Irritable bowel syndrome is a gastrointestinal disorder characterised by the presence of abdominal pain and altered bowel habits without any evidence of organic disease. The compounds of formula (I) may thus be used to alleviate pain associated with irritable bowel syndrome. The condition of a human patient suffering from irritable bowel syndrome may thus be improved.

The compounds of formula (I) may also be useful in the treatment of neurodegenerative diseases, such as Alzheimer's disease, ALS, motor neuron disease and Parkinson's disease. The compounds of formula (I) may also be useful in neuroprotection and in the treatment of neurodegeneration following stroke, cardiac arrest, pulmonary bypass, traumatic brain injury, spinal cord injury or the like.

Still further, the compounds of formula (I) are also useful in preventing or reducing dependence on, or preventing or reducing tolerance or reverse tolerance to, a dependence—inducing agent. Examples of dependence inducing agents include opioids (eg morphine), CNS depressants (eg ethanol), psychostimulants (eg cocaine) and nicotine.

There is therefore further provided by the present invention, use of a compound of formula (I) in the manufacture of a medicament for use in the treatment of a disorder substantially as hereinbefore described. The present invention further comprises a method of treating a patient suffering from, or susceptible to, a disorder substantially as hereinbefore described, which method comprises administering to the patient a therapeutically effective amount of a compound of formula (I). The term "treatment" as used herein includes the treatment of established disorders, and also includes the prophylaxis thereof.

Compounds according to the invention are particularly useful in the treatment of epilepsy and bipolar disorder, especially epilepsy.

The precise amount of the compound of formula (I) or salt thereof administered to a host, particularly a human patient, will be the responsibility of the attendant physician. However, the dose employed will depend upon a number of factors including the age and sex of the patient, the precise condition being treated and its severity, and the route of administration.

The compound of formula (I) and its salts may be administered at a dose of from 0.1 to 10 mg/kg body weight per day and more particularly 0.5 to 5 mg/kg body weight per day, calculated as the free base. The dose range for adult human beings is generally from 5 to 1000 mg/day, such as from 5 to 200 mg/day, preferably from 10 to 50 mg/day, calculated as the free base.

While it is possible for the compound of formula (I) or a pharmaceutically acceptable derivative thereof to be administered as the raw chemical, it is preferable to present it as a pharmaceutical formulation. The formulations of the present invention comprise the compound of formula (I) or a pharmaceutically acceptable derivative thereof together with one or more acceptable carriers or diluents therefor and optionally other therapeutic ingredients. The carrier(s) must be "acceptable" in the sense of being compatible with the other ingredients of the formulation and not deleterious to the recipient thereof.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compound of formula (I) or a pharmaceutically acceptable acid addition salt thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

Preferred unit dosage formulations are those containing an effective daily dose, as herein above recited, or an appropriate fraction thereof, of the active ingredient. Conveniently that may be from 5 mg to 1000 mg, more conveniently from 5 mg to 200 mg (eg. 5, 25 and 100 mg) and most conveniently 10 mg to 50 mg, calculated as the free base.

When compounds of formula (I) are used in combination with other therapeutic agents, the compounds may be administered either sequentially or simultaneously by any convenient route.

Compounds of formula (I) (which does of course also include compounds of formula (Ia) and (Ib)) and pharmaceutically acceptable salts and solvates thereof may be prepared by methods known in the art for the preparation of analogous examples. In particular, the compounds of formula (I) may be prepared by the methods outlined below and which form a further aspect of the invention. In the following processes $R^1$, $R^2$, $R^3$ and $R^4$, unless otherwise specified are as defined herein above for formula (I).

According to a general process (A), a compound of formula (I) may be prepared under suitable reaction conditions from a compound of formula (II)

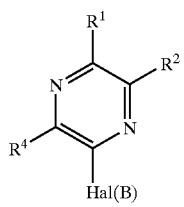

(II)

where Hal (B) represents a halogen atom, suitably chloride. For example, Hal(B) may be converted to —$NR^bR^c$ by reaction with an appropriate amine in a solvent, such as ethanol.

A compound of formula (II) may suitably be prepared from a compound of formula (III)

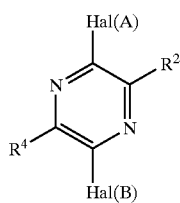

(III)

by reaction with a compound of formula (IV) $R^1B(OH)_2$. Examples of compounds of formula (IV) $R^1B(OH)_2$ include 2,3,5-trichlorobenzeneboronic acid, 2,3-dichlorobenzeneboronic acid, 2,5-dichlorobenzeneboronic acid, 1-naphthaleneboronic acid and 2-naphthaleneboronic acid. Appropriately, Hal(A) in above formula (III) is more reactive than Hal(B), and suitably Hal(A) is selected from bromide and iodide, whereas Hal(B) is aptly chloride. Compounds of formula (IV) are either commercially available or can suitably be prepared from commercially available benzene analogues e.g. 1-bromo-2,3-dichlorobenzene or 2-bromo-4,6-dichloroaniline as described herein after in greater detail in the accompanying Examples.

A compound of formula (III) can be suitably prepared by further halogenating a compound of formula (V)

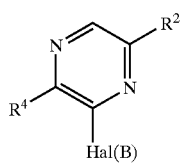

(V)

for example by reaction with a halogenating agent, such as N-bromosuccinimide, with stirring at room temperature for several hours.

A compound of formula (V) can be prepared from a di-halo compound of formula (VI)

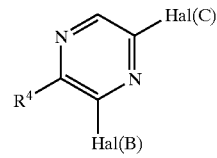

(VI)

by reaction with $R^2H$, where Hal(B) and Hal(C), which may be the same or different halogen substituents. Aptly both Hal(B) and Hal(C) are chloride. Compounds of formula (VI) are commercially available.

According to a further general process (B), a compound of formula (I) can be prepared from a compound of formula (VII)

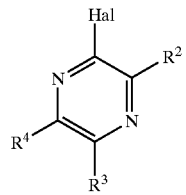

(VII)

where Hal represents a halogen atom, suitably bromide or iodide, by reaction with a compound of formula (IV) as described above.

In the case where both $R^3$ and $R^4$ represent hydrogen, a compound of formula (VII) may be commercially available. Alternatively, a compound of formula (VII) can be prepared from a compound of formula (VIII)

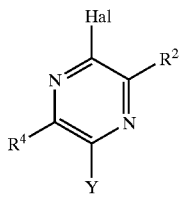

(VIII)

where Y is a group easily convertable to $R^3$. For example, in the case where Y represents $NH_2$, this can be converted to —NHC((=O))$CH_3$ by reflux in the presence of an acetylating agent, such as acetic anhydride.

A compound of formula (VIII) can be prepared from a compound of formula (IX)

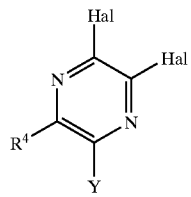

(IX)

by reaction with $R^2H$ under suitable conditions. For example a compound of formula (IX) can be reacted with ammonia in an autoclave for several hours.

A compound of formula (IX) can be prepared from a compound of formula (X)

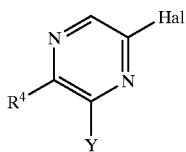

(X)

which in turn can be prepared from commercially available compounds of formula (VI) described above.

According to a further process, C, compounds of formula (I) where $R^2$ represents $NH_2$ may be prepared by cylisation and oxidation of a compound of formula (XI)

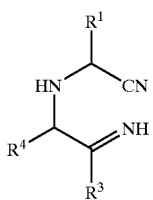

(XI)

or a salt thereof according to conventional procedures, for example by neutralising a salt of a compound of formula (XI), e.g. with lithium hydroxide in a suitable solvent such as an alcohol, e.g. methanol, under which conditions spontaneous oxidation to a compound of formula (I) occurs.

Compounds of formula (XI) may be prepared by reacting compounds of formula (XII) $R^1C(O)H$ with compounds of formula (XIII)

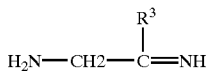

or a salt thereof, in the presence of a cyanide source, for example potassium cyanide. Compounds of formula (XII), where $R^1$ is trihalo-substituted phenyl, for example 2,3,5-trichlorobenzaldehyde, are known and may be prepared according to the methods described in WO95/07877. Compounds where $R^1$ represents alternative values are either known or may be prepared according to methods known for the preparation of known compounds.

Compounds of formula (XIII), for example aminoacetamidine, may be prepared according to known procedures, for example, those described in Chem. Berichte, 89, 1185 (1956).

According to a further process, D, compounds of formula (I) may be converted into corresponding compounds of formula (I) by employing suitable reaction techniques. For example, compounds of formula (I) wherein $R^3$ represents —NHC((=O))$R^a$ may be converted into compounds wherein $R^3$ represents —$NH_2$ by hydrolysis, for example by reaction with aqueous hydrochloric acid. In addition, compounds of formula (I) wherein $R^4$ represents hydrogen may be converted into compounds where $R^4$ represents —CN by first halogenating by reacting with a halogenating agent, such as N-bromosuccinimide, followed by reaction with a suitable source of cyanide ions, for example a mixture of sodium cyanide and copper (I) cyanide. Further, compounds of formula (I) wherein $R^4$ represents CN may be converted into compounds wherein $R^4$ represents —$CH_2OH$ via the formyl derivative which may be prepared by reacting the —CN compound with diisobutylaluminium hydride in toluene, followed by hydrolysis. The formyl derivative is then reduced to the —$CH_2OH$ compound using, for example, sodium borohydride in ethanol. Compounds wherein $R^4$ represents —$CH_2OH$ may be converted into compounds wherein $R^4$ represents —$CH_2OR^d$ by alkylation. In addition, of formula (I) wherein $R^4$ represents —CN may be converted into compounds wherein $R^4$ represents methyl via the formyl derivative, prepared as desribed above, which is then converted into the tosylhydrazone, by reaction with p-toluenesulfonhydrazide, followed by reaction with catecholborane in chloroform/tetrahydrofuran.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The following Examples which should not be construed as constituting a limitation thereto are provided to illustrate the invention.

EXAMPLE 1

2,6-Diamino-3-(2,3,5-trichlorophenyl)pyrazine 1. 2,3,5-Trichlorobromobenzene

A Sodium nitrite (3.88 g, 0.056 mole) was added in portions to concentrated sulphuric acid (28.16 ml) stirred below 10° C. A solution of 2-bromo-4,6-dichloroaniline (12 g, 0.05 mole, Lancaster) in glacial acetic acid (126 ml) was added maintaining the temperature below 10° C. The mixture was stirred below 10° C. for 1 hr and then slowly added to a stirred solution of cuprous chloride (10.11 g, 0.10 mole) in concentrated hydrochloric acid (101.05 ml) at room temperature. The mixture was then stirred at room temperature for 17 hrs. The product was filtered, washed with water (3×50 ml), dissolved in chloroform (150 ml), dried over anhydrous magnesium sulphate, filtered and the filtrate evaporated in vacuo to give the desired product. Yield 10 g (77%), M.p. 55–57° C.

2. 2,3,5-Trichlorobenzeneboronic Acid

A solution of 2,3,5-trichlorobromobenzene (8.60 g, 0.033 mole) in dry ether (33 ml) and bromoethane (4.73 ml, 7.31 g, 0.067 mole) was added dropwise to a suspension of magnesium turnings (2.80 g, 0.12 mole) in dry ether (21.50 ml) at room temperature. The mixture was refluxed for 0.50 hr and cooled to room temperature. The mixture was then added dropwise under nitrogen to a solution of trimethylborate (5.16 ml, 5.16 g, 0.05 mole) in dry ether (8.60 ml) maintaining the temperature below −60° C. This was warmed to room temperature overnight, then cooled in an ice-bath and treated with 2M hydrochloric acid (10 ml). The ether layer was separated, washed with water (2×20 ml), dried over anhydrous magnesium sulphate, filtered and the filtrate evaporated in vacuo. The residue was triturated with 40–60° C. petroleum ether, filtered and dried in vacuo. Yield 4.57 g (61%), M.p. 257–260° C.

Route A 3. 2-Chloro-6-amino-pyrazine

A suspension of 2,6-dichloropyrazine (100 g, 0.67 mole, Lancaster) in 0.880 ammonia (500 ml) was stirred and heated at 150° C. in a glass lined autoclave at 20 atm for 16 hrs. The cooled mixture was filtered, washed well with water (200 ml) and dried. The product was recrystallised from chloroform. Yield 41.98 g (48%), M.p. 150–152° C.

4. 2-Chloro-3-bromo-6-aminopyrazine and 2-amino-3-bromo-6-chloropyrazine

A solution of 2-chloro-6-aminopyrazine (20 g, 0.15 mole) in chloroform (1940 ml) was stirred at −5° C. to 0° C.

N-Bromosuccinimide (27.58 g, 0.15 mole) was added in portions maintaining the temperature between −5 and 0° C. The mixture was warmed to room temperature and stirred for 3.50 hrs. The mixture was then washed with aqueous saturated sodium bicarbonate (1×300 ml), then water (1×500 ml), dried over anhydrous magnesium sulphate, filtered and the filtrate evaporated down in vacuo. The residue was purified by 'flash chromatography' using chloroform as the eluent. Yield of 2-chloro-3-bromo-6-aminopyrazine 13.89 g (43%), M.p. 146–147° C. Yield of 2-amino-3-bromo-6-chloropyrazine 4.90 g (15%), M.p. 124–125° C.

5. 2-Amino-6-chloro-3-(2,3,5-trichlorophenyl)pyrazine

A solution of 2,3,5-trichlorobenzeneboronic acid (1.62 g, $7.18 \times 10^{-3}$ mole) in absolute ethanol (2.05 ml) was added slowly to a mixture of 2-amino-3-bromo-6 chloropyrazine (1 g, $5.1 \times 10^{-3}$ mole) and tetrakis(triphenylphospine)palladium (O) (0.334 g, $2.89 \times 10^{-4}$ mole) in benzene (10.20 ml)/2M aqueous sodium carbonate (5.50 ml). The mixture was refluxed for 17 hrs. The cooled reaction mixture was evaporated in vacuo and then extracted with chloroform (50 ml). The chloroform layer was washed with water (2×30 ml), dried over anhydrous magnesium sulphate, filtered and the filtrate evaporated down in vacuo. The residue was triturated with 40–60° C. petroleum ether, filtered and dried in vacuo. Yield 0.205 g (14%), M.p. 211–214° C.

6. 2,6-Diamino-3-(2,3,5-trichlorophenyl)pyrazine

A suspension of 2-amino-6-chloro-3-(2,3,5-trichlorophenyl)pyrazine (0.3 g, $9.71 \times 10^{-4}$ mole) in absolute ethanol (4 ml) and 0.880 aqueous ammonia (8.24 ml) was stirred and heated in an autoclave at 180° C. for 44 hrs The cooled mixture was evaporated in vacuo, and the residue extracted with chloroform (3×30 ml). The combined chloroform extracts were dried over anhydrous magnesium sulphate, filtered and the filtrate evaporated down in vacuo. The residue was purified by 'flash chromatography' using chloroform to 98:2 chloroform:methanol as the eluent. The product was triturated with 40–60° C. petroleum ether, filtered and dried in vacuo. Yield 0.155 g (56%), M.p. 178–180° C.

Route B 7. 2,6-Diamino-3-bromopyrazine

A suspension of 2-chloro-3-bromo-6-aminopyrazine (15 g, 0.072 mole) in absolute ethanol (150 ml) and 0.880 ammonia (375 ml) was stirred and heated in an autoclave at 160° C. and 20 atm. for 16 hrs The cooled mixture was evaporated in vacuo and extracted with hot methanol (3×100 ml). The combined methanol extracts were evaporated in vacuo. The residue was dissolved in hot chloroform, dried over anhydrous magnesium sulphate, filtered and the filtrate evaporated in vacuo. The residue was triturated with 40–60° C. petroleum ether, filtered, and dried in vacuo. Yield 5.51 g (40%), M.p. 176–178° C.

8. 2-Amino-3-bromo-6-acetamidopyrazine

A mixture of 2,6-diamino-3-bromopyrazine (10.509, 0.056 mole) in dry 1,1-dimethoxyethane (168 ml) and acetic anhydride (7.91 ml, 8.56 g, 0.084 mole) was refluxed under nitrogen for 2.50 hrs. The cooled mixture was evaporated in vacuo. The residue was triturated with ether, filtered and dried in vacuo Yield 10.31 g (80%), M.p. 218–221° C.

9. 2-Amino-6-acetamido-3-(2,3,5-trichlorophenyl)pyrazine

A mixture of 2-amino-3-bromo-6-acetamidopyrazine (7.00 g, 0.03 mole) in benzene (60.90 ml) and tetrakis (triphenylphosphine)palladium(0) was stirred under nitrogen at room temperature for 10 minutes. 2M aqueous sodium carbonate (30.24 ml) was added to the mixture followed by a solution of 2,3,5-trichlorobenzene boronic acid (6.83 g, 0.03 mole) in absolute ethanol (7.07 ml) and the mixture refluxed under nitrogen for 17 hrs. A further equivalent of 2,3,5-trichlorobenzene boronic acid in absolute ethanol was then added and the mixture refluxed for an additional 7.50 hrs. Finally, another equivalent of 2,3,5-trichlorobenzene boronic acid in absolute ethanol was added to the mixture and continued refluxing for 17 hrs. The cooled mixture was evaporated in vacuo. The residue was dissolved in chloroform (150 ml), washed with aqueous saturated sodium bicarbonate (1×100 ml) and water (1×100 ml), dried over anhydrous magnesium sulphate, filtered and the filtrate evaporated down in vacuo. The residue was purified by 'flash chromatography' using chloroform to 98:2 chloroform:methanol as the eluent. Yield 3.02 g (30%), M.p. 200–203° C.

10. 2,6-Diamino-3-(2,3,5-trichlorophenyl)pyrazine

A suspension of 2-amino-6-acetamido-3-(2,3,5-trichlorophenyl)pyrazine (2.97 g, $8.96 \times 10^{-3}$ mole) in 12M hydrochloric acid (1.31 ml) and water (4.04 ml) was fluxed for 1.75 hrs. The cooled mixture was then basified with 0.880 aqueous ammonia (5 ml) and extracted with chloroform (3×50 ml). The combined chloroform extracts were dried over anhydrous magnesium sulphate, filtered and the filtrate evaporated down in vacuo at 80° C. Yield 2.29 g (88%), M.p. 178–180° C.

Route C 11. 2-{[Cyano-(2,3,5-trichlorophenyl)-methyl]-amino}-acetamidine hydrobromide Aminoacetamidine dihydrobromide (162.1 g, 0.774 mole) was added in portions to a solution of 2,3,5-trichlorobenzaldehyde (200.0 g, 0.851 mole) in methanol (2.43 liters) at room temperature. Once the addition was complete potassium cyanide (50.4 g, 0.774 mole) was added in one portion to the resulting mixture. The suspension was then stirred at 25° C. for 4 hours before being warmed to 50° C. The mixture is stirred at 50° C. for 24 hours. Methanol was then removed in vacuo, the resulting solid was slurried in water (1.5 liters) and ethyl acetate (2.5 liters) and collected by filtration. The solid was then dried in vacuo at 50° C. overnight to give the desired product. Yield 96.31 g (33.4%), $^1$H nm, (d-6 DMSO) δ/ppm 8.72 (3H, br, NH); 7.99 (1H, d, J 2.3 Hz, ArH); 7.79 (1H, d, J 2.3 Hz, ArH); 5.39 (1H, d, J 10.6 Hz, ArCH(CN)NH); 4.35 (1H, m, ArCH(CN)NH); 3.56 (2H, d, J 6.4 Hz, ArCH(CN)NHCH$_2$C(=NH)NH$_2$).

12. 2,6-Diamino-3-(2,3,5-trichlorophenyl)pyrazine

2-{[Cyano-(2,3,5-trichlorophenyl)-methyl]-amino}-acetamidine hydrobromide (95.36 g, 0.256 mole) was added in portions to a solution of lithium hydroxide monohydrate (16.11 g, 0.384 mole) in methanol (1.9 liters) at room temperature. The resulting solution was stirred at room temperature for 3 hours before being evaporated to dryness in vacuo. The resulting solid was slurried in water (1.15 liters) and collected by filtration. After drying at 50° C. in vacuo the crude material was purified by recrystallisation from toluene to give the desired product. Yield 69.51 g (93.8%), M.p. 178–180° C.

EXAMPLE 2

2,6-Diamino-3-(2,3-dichlorophenyl)pyrazine 1. 2,3-Dichlorobenzeneboronic Acid

A solution of 1-bromo-2,3-dichlorobenzene (20 g, 0.088 mole, Aldrich) in dry tetrahydrofuran (44.24 ml) was added dropwise to a solution of n-butyllithium (1.6M in hexane, 66.36 ml, 0.11 mole) in anhydrous tetrahydrofuran (16 ml), maintaining the temperature below −65° C. The resulting pale yellow suspension was stirred at −78° C. for 75 min. Trimethylborate (13.28 ml, 12.16 g, 0.12 mole) was added dropwise maintaining the temperature below −55° C. The resulting pale yellow solution was warmed to room temperature overnight. Excess n-butyllithium was decomposed with water (30 ml) and the reaction mixture was evaporated in vacuo. The residue obtained was suspended in water and acidified with 2M hydrochloric acid (10 ml). The insoluble solid was filtered, washed well with water and dried. The solid was suspended in 60–80° C. petroleum ether, stirred at room temperature for 10 min, filtered dried in vacuo. Yield 8.42 g (50%), M.p. 235–238° C.

2. 2-Amino-6-chloro-3-(2,3-dichlorophenyl)pyrazine

This compound was prepared in an analogous manner to Example 1 Route A, from 2-amino-3-bromo-6-chloropyrazine. Yield 0.343 g (26%), M.p. 179–181° C.

3. 2,6-Diamino-3-(2,3-dichlorophenyl)pyrazine

This compound was prepared in an analogous manner to Example 1 Route A, from 2-amino-6-chloro-3-(2,3-dichlorophenyl)pyrazine, by reaction with 0.880 ammonia. Yield 0.195 g, M.p. 169–170° C.

EXAMPLE 3

2,6-Diamino-3-(2,5-dichlorophenyl)pyrazine 1. 2,5-Dichlorobenzeneboronic Acid

This compound was prepared in an analogous manner to the compound in Example 2 from 2,5-dichlorobromobenzene (Aldrich). Yield 2.19 g (55%), M.p. 278–280° C.

2. 2-Amino-6-acetamido-3-(2,5-dichlorophenyl)pyrazine

This compound was prepared in an analogous manner to Example 1 Route B, from 2-amino-3-bromo-6-acetamidopyrazine. Yield 0.45 g, M.p. 152–154° C.

3. 2,6-Diamino-3-(2,5-dichlorophenyl)pyrazine

This compound was prepared in an analogous manner to Example 1 Route B, from 2-amino-6-acetamido-3-(2,5-dichlorophenyl)pyrazine. Yield 0.123 g, M.p. 159–160° C.

EXAMPLE 4

2,6-Diamino-(1-naphthalene)pyrazine 1. 2-Amino-6-chloro-3-(1-naphthalene)pyrazine This compound was prepared in an analogous manner to Example 1 Route A, from 2-amino-3-bromo-6-chloropyrazine and 1-naphthaleneboronic acid (Lancaster). Yield 0.709 g (58%), M.p. 138–139° C.

2. 2,6-Diamino-(1-naphthalene)pyrazine

This compound was prepared in an analogous manner to Example 1 Route A, from 2-amino-6-chloro-3-(1-naphthalene)pyrazine by reaction with 0.880 ammonia. Yield 0.167 g (50%), M.p. 180–183° C.

EXAMPLE 5

2,6-Diamino-3-(2-naphthalene)pyrazine 1. 2-Naphthaleneboronic Acid

This compound was prepared in an analogous manner to the compound in Example 2 from 2-bromonaphthalene (Aldrich). Yield 1.71 g (40%), M.p. 280–282° C.

2. 2-Amino-6-acetamido-3-(2-naphthalene)pyrazine

This compound was prepared in an analogous manner to Example 1 Route B, from 2-amino-3-bromo-6-acetamidopyrazine. Yield 0.46 g, M.p. 235–237° C.

3. 2,6-Diamino-3-(2-naphthalene)pyrazine

This compound was made in an analogous manner to Example 1 Route B, from 2-amino-6-acetamido-3-(2-naphthalene)pyrazine. Yield 0.121 g, M.p. 168–70° C.

EXAMPLE 6

2-Amino-6-(4-methyl-1-piperazinyl)-3-(2,3,5-trichlorophenyl)pyrazine

2-Amino-6-chloro-3-(2,3,5-trichlorophenyl)pyrazine (0.215 g, $7.0 \times 10^{-3}$ mole) Example 1 Route A and 1-methylpiperazine (5 ml, Aldrich), were heated at 140° C. for 1 hr. The mixture was evaporated in vacuo and the residue was purified by 'flash chromatography' eluting with ethanol:dichloromethane, 0–4%. The product was dissolved in the minimum of dichloromethane and hexane (10 ml), added slowly to give yellow needles. Yield 0.247 g (95%), M.p. 185° C.

EXAMPLE 7

2-Amino-6-dimethylamino-3-(2,3-dichlorophenyl)pyrazine

This compound was prepared in an analogous manner to the compound in Example 6 from 2-amino-6-chloro-3-(2,3-dichlorophenyl)pyrazine (Example 2) and dimethylamine (Aldrich). M.p. 147–148° C.

EXAMPLE 8

2-Amino-6-dimethylamino-3-(1-naphthalene)pyrazine

This compound was prepared in an analogous manner to the compound in Example 6 from 2-amino-6-chloro-3-(1-naphthalene)pyrazine (Example 4). M.p. 131° C.

EXAMPLE 9

2,6-Dicyclopropylcarbonylamino-3-(2,3,5-trichlorophenyl)pyrazine and 2-Amino-6-cyclopropylcarbonylamino-3-(2,3,5-trichlorophenyl)pyrazine Anhydrous pyridine (0.137 ml), 4-dimethylaminopyridine (0.114 g) and cyclopropanecarbonylchloride (0.33 g, 0.286 ml, $3.14 \times 10^{-3}$ mole, Aldrich) were added to a solution of 2,6-Diamino-3-(2,3,5-trichlorophenyl)pyrazine (Example 1), in anhydrous tetrahydrofuran (12 ml) and the resulting reaction mixture was refluxed at 90° C. for 2.50 hrs. The suspension obtained was cooled to room temperature and evaporated in vacuo. The residue was extracted with ethylacetate (3×20 ml), washed with water (2×20 ml), dried over anhydrous magnesium sulphate, filtered and the filtrate evaporated in vacuo. The residue was purified by 'flash chromatography' using 15:25 to 5:35, hexane:ether, as the eluent. Yield of 2,6-dicyclopropylcarbonylamino-3-(2,3,5-trichlorophenyl)pyrazine 0.340 g (51%), M.p. 212–214° C. Yield of 2-amino-6-cyclopropylcarbonylamino-3-(2,3,5-trichlorophenyl)pyrazine 0.174 g (31%), M.p. 240–244° C.

EXAMPLE 10

2,6-Diisopropylcarbonylamino-3-(2,3,5-trichlorophenyl)pyrazine and 2-Amino-4-isopropylcarbonylamino-3-(2,3,5-trichlorophenyl)pyrazine These compounds were prepared in an analogous manner to Example 9 from 2,6-diamino-3-(2,3,5-trichlorophenyl)pyrazine (Example 1), by reaction with isobutyrylchloride (Aldrich). Yield of 2,6-diisopropylcarbonylamino-3-(2,3,5-trichlorophenyl) pyrazine 0.313 g (46%), M.p. 227–229° C. Yield of 2-amino-6-isopropylcarbonylamino-3-(2,3,5-trichlorophenyl)pyrazine 0.166 g (29%), M.p. 230–232° C.

EXAMPLE 11

2-isopropylcarbonylamino-6-amino-3-(2,3,5-trichlorophenyl)pyrazine 1. 2-isopropylcarbonylamino-6-acetamido-3-(2,3,5-trichlorophenyl)pyrazine This compound was prepared in an analogous manner to Example 9 from 2-amino-6-acetamido-3(2,3,5-trichlorophenyl)pyrazine (Example 1) and one equivalent isobutyrylchloride (Aldrich). Yield 0.120 g M.p. 230–232° C.

2. 2-isopropylcarbonylamino-6-amino-3-(2,3,5-trichlorophenyl)pyrazine

Stannous chloride (0.182 g, 0.0096 mole) was added to the suspension of 2-isopropylcarbonylamino-6-acetamido- 3-(2,3,5-trichlorophenyl)pyrazine (0.13 g, 3.24×10$^{-4}$ mole), in absolute ethanol (6.50 ml) and the resulting mixture stirred at 50–60° C. for 1 hr 20 min. The reaction mixture was cooled and evaporated in vacuo. The residue was extracted with ethylacetate (3×20 ml), washed with water (2×20 ml), dried over anhydrous magnesium sulphate, filtered and the filtrate evaporated in vacuo. The residue was purified by 'flash chromatography' using chloroform:methanol, 99:1 as the eluent. Yield 0.046 g (40%), M.p. 105–108° C.

EXAMPLE 12
2-Cyclopropylcarbonylamino-6-amino-3-(2,3,5-trichlorophenyl)pyrazine 1. 2-Cyclopropylcarbonylamino-6-acetamido-3-(2,3,5-trichlorophenyl)pyrazine This compound was prepared in an analogous manner to Example 9 from 2-amino-6-acetamido-3-(2,3,5-trichlorophenyl)pyrazine (Example 1) and cyclopropylcarbonyl chloride (Aldrich). Yield 0.387 g (61%) N.m.r. (D6DMSO) δ: 0.53 (2H, m), 0.7 (2H, m), 1.75 (1H, m), 2.18 (3H, s), 7.43 (1H, d), 7.87 (1H, d), 9.22 (1H, s), 10.36 (1H, b), 10.83 (1H, b).

2. Cyclopropylcarbonylamino-6-amino-3-(2,3,5-trichlorophenyl)pyrazine

This compound was prepared in an analogous manner to Example 11 from 2-cyclopropylcarbonylamino-6-acetamido-3-(2,3,5-trichlorophenyl)pyrazine. Yield 0.120 g (35%), M.p. 188–190° C.

EXAMPLE 13
2-Amino-3-(2,3,5-trichlorophenyl)pyrazine

A solution of 2,3,5-trichlorobenzeneboronic acid (1.54 g, 6.82 mmol) in absolute ethanol (1–5 ml) was added slowly to a mixture of 2-amino-3-chloropyrazine (0.589 g, 4.54 mmol) and tetrakis(triphenylphosphine)palladium(0) (0.299 g, 0.259 mmol) in benzene (10.5 ml)/2M aqueous sodium carbonate (4.54 ml). The mixture was refluxed for 17 hours. The cooled reaction mixture was partitioned between water and ethylacetate (50 ml). The organic layer was washed with water (2×30 ml), dried (MgSO$_4$) and evaporated. The crude product was purified by flash chromatography using chloroform to 0.5%methanol/chloroform as the eluent. The product was then crystallised from 40–60 petrol. Yield 0.15 g, 12% M.p. 142–143° C.

EXAMPLE 14
2-Amino-6-acetamido-3-(2,3,5-trichlorophenyl)pyrazine

Prepared as described hereinbefore (see example 1.9).

EXAMPLE 15
2-Amino-6-acetamido-3-(2,5-dichlorophenyl)pyrazine

Prepared as described hereinbefore (see example 3.2).

EXAMPLE 16
2-Amino-6-acetamido-3-(2-naphthalene)pyrazine

Prepared as described hereinbefore (see example 5.2)

EXAMPLE 17
5-Cyano-2,6-Diamino-3-(2,3,5-trichlorophenyl)pyrazine 1. 5-Bromo-2,6-Diamino-3-(2,3,5-trichlorophenyl)pyrazine N-Bromosuccinimide (0.194 g, 1.09×10$^{-3}$ mole) was added over 20 min to a mixture of 2,6-Diamino-3-(2,3,5-trichlorophenyl)pyrazine (0.3 g, 1.04×10$^{-3}$ mole) in dimethylsulfoxide (10 ml) and water (0.25 ml) below 15° C. The resulting reaction mixture was stirred at 15° C. for 1 hr, poured onto ice water (150 ml) and extracted with ethyl acetate (2×75 ml). The extract was then washed with 2 M sodium carbonate solution (50 ml) and water (100 ml), dried over anhydrous magnesium sulphate, filtered and the filtrate evaporated in vacuo. The residue was purified by 'flash chromatography' using 5–13% ethyl acetate in cyclohexane as the eluent. Yield 0.183 g (48%), M.p. 222–224° C.

2. 5-Cyano-2,6-Diamino-3-(2,3,5-trichlorophenyl)pyrazine

A mixture of 97% sodium cyanide (0.064 g, 1.306×10$^{-3}$ mole) and 90% copper(I) cyanide (0.135 g, 1.306×10$^{-3}$ mole) in dry dimethylformamide (5 ml) was stirred and heated to 130° C. To the resulting clear solution was added 5-Bromo-2,6-Diamino-3-(2,3,5-trichlorophenyl)pyrazine (0.35 g, 0.95×10$^{-3}$ mole) in small portions, and the solution was maintained at 140–150° C. for 16 hrs. The reaction mixture was cooled and evaporated in vacuo. The residue was extracted with ethyl acetate (100 ml), washed with water (100 ml) and brine (100 ml), dried over anhydrous magnesium sulphate, filtered and the filtrate evaporated in vacuo. The residue was purified by 'flash chromatography' using 5–17% ethyl acetate in cyclohexane as the eluent. Yield 0.152 g (51%), M.p. 277–279° C. Anal. Calcd for $C_{11}H_6N_5Cl_3$ 0.02 $C_6H_{12}$: C, 42.23; H, 1.99; N, 22.15. Found: C, 42.36; H, 1.78; N, 21.79.

EXAMPLE 18
5-Hydroxymethyl-2,6-Diamino-3-(2,3,5-trichlorophenyl)pyrazine 1. 5-Formyl-2,6-Diamino-3-(2,3,5-trichlorophenyl)pyrazine Diisobutylaluminium hydride (1.5 M in toluene) (2.12 ml, 3.18×10$^{-3}$ mole) was added dropwise at 0° C. under nitrogen to a suspension of 5-Cyano-2,6-Diamino-3-(2,3,5-trichlorophenyl)pyrazine (0.5 g, 1.59×10$^{-3}$ mole) in dry toluene (70 ml) and the reaction was stirred at 0° C. for 1 hr. A further one equivalent of diisobutylaluminium hydride was then added and the mixture again stirred at 0° C. for 1 hr. Methanol (1 ml) was added carefully at 0° C. under nitrogen to destroy excess hydride and the reaction was warmed to room temperature. Ethyl acetate (100 ml) was added and the solution was washed with 5% citric acid solution (2×100 ml). The organic layer was separated, washed with brine (100 ml), dried over magnesium sulphate, filtered and the filtrate evaporated in vacuo to give the desired product. Yield 0.340 g (67%), N.m.r. (D6DMSO) δ: 7.53 (1H, d), 7.91 (1H, d), 6.90–7.80 (4H, b), 9.49 (1H, s).

2. 5-Hydroxymethyl-2,6-Diamino-3-(2,3,5-trichlorophenyl)pyrazine

To a stirred solution of 5-Formyl-2,6-Diamino-3-2,3,5-trichlorophenyl)pyrazine (0.198 g, 6.24×10$^{-4}$ mole) in ethanol (100 ml) was added sodium borohydride (0.035 g, 9.35×10$^{-4}$ mole) at room temperature. The reaction was stirred at room temperature under nitrogen for 1 hr, water (1 ml) was added and the solution evaporated in vacuo. The residue was dissolved in ethyl acetate (200 ml), washed with brine, dried over magnesium sulphate, filtered and evaporated in vacuo. The product was purified by 'flash chromatography' using 1140% ethyl acetate in cyclohexane as the eluent. Yield 0.104 g (52%), M.p. 185–186° C. N.m.r. (D6DMSO) δ: 4.32 (2H, d), 4.98 (1H, t), 5.56 (2H, s), 5.85 (2H, s), 7.30 (1H, d), 7.76 (1H, d).

EXAMPLE 19
5-Methyl-2,6-Diamino-3-(2,3,5-trichlorophenyl)pyrazine 1. 5-Formyl-2,6-Diamino-3-(2,3,5-trichlorophenyl)pyrazine, tosylhydrazone 5-Formyl-2,6-Diamino-3-(2,3,5-trichlorophenyl)pyrazin (0.330 g, 1.04×10$^{-3}$ mole) was added to a solution of p-toluenesulfonhydrazide (0.3 g, 1.61×10$^{-3}$ mole) in methanol (50 ml). The solution was refluxed under nitrogen for 4 hrs, cooled to room temperature and the solvent evaporated in vacuo. The residue was purified via 'flash chromatography' using 0–30% ethyl acetate in cyclohexane as the eluent. Yield 0.270 g (53%)

Mass Spec: (electrospray) 487 (MH$^+$)
Retention Time 3.33 minutes
Micromass Platform Series 2
5 min Grad. (2 mmABZ)
Instrument: Red Flow rate: 0.8 ml/min
Eluents
A—0.1%V/V Formic Acid+10 mmol Ammonium Acetate
B—95% MeCN+0.05% V/V Formic Acid
Column: 5 cm×2.1 mm ID ABZ+PLUS
Inject Vol: 5 µl Temp: RT

| Time | A % | B % |
|------|-----|-----|
| 0.00 | 100 | 0 |
| 3.50 | 0.0 | 100 |
| 5.00 | 0.0 | 100 |
| 5.50 | 100 | 0 |

2. 5-Methyl-2,6-Diamino-3-(2,3,5-trichlorophenyl)pyrazine

Catecholborane (1.0 M in tetrahydrofuran) (1.09 ml, 1.09×10$^{-3}$ mole) was added dropwise at 0° C. under nitrogen to a suspension of 5-tosylhydrazone-2,6-diamino-3-(2,3,5-trichlorophenyl)pyrazine (0.265 g, 5.46×10$^{-4}$ mole) in dry chloroform (15 ml) and tetrahydrofuran (20 ml). The reaction was stirred at 0° C. for 1 hr, quenched and sodium acetate trihydrate (g, 5.46×10$^{-4}$ mole) was added. The mixture was warmed to room temperature, stirred for 1 hr and the solvents evaporated in vacuo. The residue was dissolved in ethyl acetate (100 ml), washed with 5% sodium carbonate solution, then water, dried over anhydrous magnesium sulphate, filtered and the filtrate evaporated in vacuo. The residue was purified via 'flash chromatography' using 10–25% ethyl acetate in cyclohexane as the eluent. Yield 0.017 g (10%), N.m.r. (CDCl$_3$) δ: 2.35 (3H, s), 4.10 (2H, b), 4.45 (2H, b), 7.35 (1H, d), 7.52 (1H, d).

Mass Spec: (electrospray) 305 (MH$^+$)
Retention Time 2.89 minutes
(Conditions as for Example 19.1)

PHARMACY EXAMPLES
Sterile Formulations

Example A

| | mg/ml |
|---|---|
| Compound of the Invention | 0.1 mg |
| Sodium Chloride USP | 9.0 mg |
| Water for Injection USP qs to | 1 ml |

The components are dissolved in a portion of the water for injections and the solution made up to a final volume to provide 0.1 mg/ml of the compound of the Invention. Where a salt of the compound is used the quantity of compound is increased to provide 0.1 mg/ml of the free base. The solution may be packaged for injection, for example by filling and sealing into ampoules, vials or syringes These may be aseptically filled and/or terminally sterilised by, for example, autoclaving at 121° C.

Further sterile formulations may be prepared in a similar manner to obtain alternative concentrations of the compound.

Example B

| | mg/ml |
|---|---|
| Compound of the Invention | 0.5 mg |
| Mannitol | 50.0 mg |
| Water for Injections qs to | 1.0 ml |

Dissolve the components in a portion of the Water for Injections. Make up to final volume and mix until homogeneous. Filter formulation through a sterilising filter and fill into glass vials. Lyophilise and seal vials. Reconstitute with appropriate solvent prior to use.

Formulations for Oral Administration

Tablets may be prepared by the normal methods such as direct compression or wet granulation. The tablets may be film coated with suitable film forming materials, such as an Opadry, using standard techniques. Alternatively the tablets may be sugar coated.

Example C

Direct Compression Tablet

| | mg/Tablet |
|---|---|
| Compound of the Invention | 5.0 mg |
| Magnesium Stearate | 4.0 mg |
| Microcrystalline Cellulose (Avicel PH102) qs to | 400.0 mg |

The compound of the Invention is passed through a 30 mesh sieve and blended with the Avicel and Magnesium Stearate. The resultant blend is compressed into tablets using a suitable tablet press fitted with 11.0 mm diameter punches so as to provide 5 mg of the Compound of the Invention per tablet. Tablets of other strengths, containing for example 25 or 100 mg/tablet of the Compound of the Invention may be prepared in a similar manner.

Example D

Wet Granulation Tablet

| | mg/Tablet |
|---|---|
| Compound of the Invention | 5.0 mg |
| Pregelled Starch | 28.0 mg |
| Sodium Starch Glycollate | 16.0 mg |
| Magnesium Stearate | 4.0 mg |
| Lactose qs | 400.0 mg |

The Compound of the Invention, Lactose, Pregelled Starch and Sodium Starch Glycollate were dry mixed and then granulated using a suitable volume of Purified Water. The resultant granules were dried and then blended with the Magnesium Stearate. The dried granules were compressed using a suitable tablet press fitted with 11.0 mm diameter punches so as to provide 5 mg of the Compound of the Invention per tablet.

Tablets of other strengths such as 25 and 100 mg/tablet were prepared.

Example E

Hard Gelatin Capsule

|  | mg/capsule |
| --- | --- |
| Compound of the Invention | 5.0 mg |
| Microcrystalline Cellulose (Avicel PH102) qs | 700.0 mg |

The Compound of the Invention is passed through a 30 mesh sieve and then blended with the Microcrystalline Cellulose to provide an homogeneous blend. The blend may then be filled into size OEL hard gelatin capsule shells so as to provide capsules containing 5.0 mg/capsule of Compound of the Invention. Alternative strengths such as 25 or 100 mg/capsule of Compound of the Invention may be made in a similar manner.

Example F

Soft Gelatin Capsule

|  | mg/capsule |
| --- | --- |
| Compound of the Invention | 10.0 mg |
| Polyethylene Glycol | 90.0 mg |
| Propylene Glycol qs | 200.0 mg |

Blend together the Polyethylene Glycol and Propylene Glycol using heat as necessary. Stir until homogeneous. Add the Compound of the Invention and mix until homogeneous. Fill into an appropriate gelatin mass to give soft gelatin capsules containing 200 mg of the formulation, to provide 10.0 mg/capsule of the Compound of the Invention.

Alternative strengths, for example, 5 and 25 mg/capsule of the Compound of the Invention may be prepared in a similar manner.

Example G

Syrup

| Compound of the Invention | 5.0 mg |
| --- | --- |
| Sorbitol Solution | 1500.0 mg |
| Glycerol | 1000.0 mg |
| Sodium Benzoate | 5.0 mg |
| Flavour | 12.5 mg |
| Purified Water qs to | 5.0 ml |

The Sodium Benzoate is dissolved in a portion of the purified water and the Sorbitol Solution added. The Compound of the Invention, Flavour and Glycerol are added and mixed until homogeneous. The resultant mixture is made up to volume with the purified water.

Other Formulations

Example H

Suppository

|  | mg/suppository |
| --- | --- |
| Compound of the Invention | 10.0 mg |
| Witepsol W32, hard fat qs | 2000.0 mg |

Melt the Witepsol W32 at approximately 36° C. To a portion of this add the Compound of the Invention and blend. Incorporate the remaining melted Witepsol W32 and blend until homogeneous. Fill mould with 2000 mg of the formulation to provide 10.0 mg/suppository of the Compound of the Invention.

Example I

Transdermal

| Compound of the Invention | 5.0 mg |
| --- | --- |
| Silicone Fluid | 90.9 mg |
| Colloidal Silicone Dioxide | 5.0 mg |

Mix the silicone fluid and active together and add the colloidal silicone dioxide. The material is then dosed into a subsequently heat sealed polymeric laminate comprised of the following: polyester release finer, skin contact adhesive composed of silicone or acrylic polymers, a a control membrane which is a polyolefin (foe example polyethylene or polyvinyl acetate) or polyurethane, and an impermeable backing membrane of a polyester multilaminate.

Biological Data

Compounds of the invention have been shown to have antiepileptic activity by, for example, their ability to inhibit hind limb extension in the supra maximal electro shock model. Male Han Wistar rats (150–200 mg) are dosed i.p. with a suspension of test compound in 0.25% methylcellulose 2 hr prior to test. A visual observation is carried out just prior to testing for the presence of ataxia. Using auricular electrodes a current of 200 mA, duration 200 millisec, is applied and the presence or absence of hind limb extension is noted.

Compounds according to the invention exibited $ED_{50}$'s in the range of 1 to 20 mg/kg when tested in the above test.

No apparent adverse or toxic effects were observed during the above in vivo test due to the administration of the compounds of the invention.

What is claimed is:

1. A method of treating a patient suffering from bipolar disorder, pain, or functional bowel disorder, said method comprising administering an effective amount of a compound of formula (I)

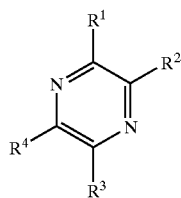
(I)

wherein
- $R^1$ is selected from the group consisting of phenyl substituted by one or more halogen atoms, naphthyl and naphthyl substituted by one or more halogen atoms;
- $R^2$ is selected from the group consisting of —$NH_2$ and —NHC(=O)$R^a$;
- $R^3$ selected from the group consisting of —$NR^bR^c$, —NHC(=O) $R^a$ and hydrogen;
- $R^4$ is selected from the group consisting of hydrogen, —$C_{1-4}$ alkyl, —CN, —$CH_2OH$, —$CH_2OR^d$, —$CH_2S(O)_xR^d$ and —$C_{1-4}$ alkyl substituted by one or more halogen atoms;

wherein
- $R^a$ represents $C_{1-4}$ alkyl or $C_{3-7}$ cycloalkyl, and
- $R^b$ and $R^c$, which may be the same or different, are selected from hydrogen and $C_{1-4}$ alkyl, or together with the nitrogen atom to which they are attached, form a 6-membered saturated heterocycle having one nitrogen atom or $NR^bR^c$ form a piperazinyl ring which heterocycles can be further substituted with one or more $C_{1-4}$ alkyl;
- $R^d$ is selected from $C_{1-4}$ alkyl or $C_{1-4}$ alkyl substituted by one or more halogen atoms;
- x is an integer zero, one or two;

and salts, thereof;

with the proviso that $R^1$ does not represent

when $R^2$ is —$NH_2$, and both $R^3$ and $R^4$ are hydrogen.

2. A method according to claim 1 wherein $R^1$ is phenyl substituted by one or more halogen atoms.

3. A method according to claim 2 wherein $R^1$ is 2,3,5-trichlorophenyl.

4. A method according to claim 1 wherein $R^2$ and $R^3$ are —$NH_2$.

5. A method according to claim 1 wherein $R^4$ is hydrogen or —$CH_2OH$.

6. A method according to claim 5 wherein $R^4$ is hydrogen.

7. The method of claim 1 wherein the compound is 2,6-diamino-3-(2,3,5-trichlorophenyl)pyrazine and salts thereof.

* * * * *